US006668186B1

(12) United States Patent
Zavislan et al.

(10) Patent No.: US 6,668,186 B1
(45) Date of Patent: *Dec. 23, 2003

(54) CELLULAR SURGERY UTILIZING CONFOCAL MICROSCOPY

(75) Inventors: James M. Zavislan, Pittsford, NY (US); Roger J. Greenwald, Holley, NY (US)

(73) Assignee: Lucid, Inc., Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/438,065

(22) Filed: Nov. 10, 1999

Related U.S. Application Data

(63) Continuation of application No. 09/044,355, filed on Mar. 19, 1998, now Pat. No. 5,995,867.
(60) Provisional application No. 60/041,050, filed on Mar. 19, 1997.

(51) Int. Cl.[7] .............................. A61B 6/00; A61B 18/18
(52) U.S. Cl. ............................... 600/476; 606/2; 606/10
(58) Field of Search .................................. 600/476, 473; 382/133; 356/317, 318, 303; 606/2, 9, 11, 13, 17; 250/461.2

(56) References Cited

U.S. PATENT DOCUMENTS

| 4,395,397 | A | | 7/1983 | Shapiro |
| 4,408,602 | A | * | 10/1983 | Nakajima ..................... 606/10 |
| 5,034,613 | A | | 7/1991 | Denk et al. |
| 5,035,693 | A | | 7/1991 | Kratzer et al. |
| 5,065,008 | A | | 11/1991 | Hakamata et al. |
| 5,089,384 | A | | 2/1992 | Hale |
| 5,200,838 | A | * | 4/1993 | Nudelman et al. .......... 358/443 |
| 5,364,390 | A | * | 11/1994 | Taboada et al. ............... 606/10 |
| 5,458,594 | A | | 10/1995 | Mueller et al. |
| 5,493,116 | A | | 2/1996 | Toro-Lira et al. |
| 5,501,655 | A | | 3/1996 | Rolt et al. |
| 5,582,168 | A | | 12/1996 | Samuels et al. |
| 5,608,519 | A | | 3/1997 | Gourley et al. |
| 5,632,741 | A | | 5/1997 | Zavislan et al. |
| 5,653,706 | A | | 8/1997 | Zavislan et al. |
| 5,753,230 | A | | 5/1998 | Brooks et al. |
| 5,760,950 | A | * | 6/1998 | Maly et al. .................. 359/368 |
| 5,784,162 | A | | 7/1998 | Cabib et al. |
| 5,788,639 | A | | 8/1998 | Zavislan et al. |
| 5,848,177 | A | * | 12/1998 | Bauer et al. ................... 38/128 |
| 5,995,866 | A | * | 11/1999 | Lemelson .................... 600/476 |
| 5,995,867 | A | * | 11/1999 | Zavislan et al. ............. 600/476 |
| 6,099,522 | A | * | 8/2000 | Knopp et al. .................. 606/10 |
| 6,166,385 | A | * | 12/2000 | Webb et al. ............. 250/458.1 |

* cited by examiner

Primary Examiner—Shawna J. Shaw
(74) Attorney, Agent, or Firm—Kenneth J. Lukacher; Martin Lukacher

(57) ABSTRACT

An improved system for cellular surgery which includes a laser for producing a laser beam, and confocal optics for scanning and focusing the laser beam in tissue and generating confocal images of the tissue in accordance with returned light from the tissue. The confocal images are visualized on a display. The system includes a controller for enabling the operator to select one or more cells of the tissue in the displayed confocal images for surgical treatment. The controller operates the laser and confocal optics in a first mode to treat the tissue when the confocal optics focus the laser beam at least one region associated with the selected cells in the tissue, but at all other times operates the laser and confocal optics in a second mode which does not damage the tissue. The treatment may be localized to concentrate the energy of the laser to the region including the selected cell or cells, or the treatment may be non-localized to distribute the energy of the laser to the region which includes the selected cell(s) and also the cells of the tissue surrounding such selected cell(s). In another embodiment, an apparatus is provided having a confocal imaging system, which focuses a first laser beam through confocal optics to tissue and provides confocal images of the tissue, and a treatment system which focuses a second laser beam through the confocal optics coaxial with the first laser beam for treating at one or more selected locations in the imaged tissue.

9 Claims, 3 Drawing Sheets

CELLULAR SURGERY UTILIZING CONFOCAL MICROSCOPY

DESCRIPTION

This application is a continuation of application Ser. No. 09/044,355, filed now U.S. Pat. No. 5,995,867 issue Mar. 19, 1998, which claims the benefit of priority from U.S. Provisional Application Serial No. 60/041,050, filed Mar. 19, 1997.

FIELD OF THE INVENTION

The present invention relates to a system (method and apparatus) for cellular surgery utilizing confocal microscopy, and relates particularly to, a system for cellular surgery which provides for confocal imaging of tissue and treatment of one or more cells of the tissue being imaged. Cellular surgery is herein defined as surface or subsurface excision, ablation, thermolysis, photo-drug activation, or photo-chemical or photo-acoustical changes, on a region of tissue characterized by one or more individual cells.

BACKGROUND OF THE INVENTION

Confocal microscopy involves scanning tissue to produce microscopic sectional images of surface or subsurface tissue. Such microscopic imaged sections may be made in-vivo and can image at cellular resolutions. Examples of confocal scanning microscopes are found in U.S. Pat. No. 5,788,639, issued Aug. 4, 1998 to James M. Zavislan, and in Milind Rajadhyaksha et al., "In vivo Confocal Scanning Laser Microscopy of Human Skin: Melanin provides strong contrast," The Journal of Investigative Dermatology, Volume 104, No. 6, June 1995, pages 1–7. For further information concerning the system of the Zavislan application, see Milind Rajadhyaksha and James M. Zavislan, "Confocal laser microscope images tissue in vivo," Laser Focus World, February 1997, pages 119–127. These systems have confocal optics which direct light to the patient's tissue and image the returned reflected light. These confocal systems although useful for examination of lesions or other diseased tissue have no capability for treatment of cells, such as, for example, to cause thermolysis, photolysis, or ablation of imaged cells.

An optical microscope apparatus has been proposed for targeting a laser beam to a cell, as described in U.S. Pat. No. 4,289,378, which utilizes a visible marker laser beam and a non-visible working laser beam focused to different spots of a cell of an in-vitro sample. This device however does not use confocal microscopy for tissue imaging and does not provide treatment of cells of in-vivo tissue of a patient.

A microsurgical instrument with electronic visualization of tissue being treated is described in U.S. Pat. No. 5,653,706, in which energy from a single laser is applied to selected locations under skin to provided localized photo-thermolysis of tissue at such locations. Visualization of the tissue is provided by a CCD video camera in the instrument. Confocal microscopy is not utilized for tissue imaging.

SUMMARY OF THE INVENTION

Accordingly, the principal object of the present invention is to provide an improved system for generating confocal images of in-vivo tissue which enables surgical treatment of tissue being imaged.

A further object of the present invention is to provide an improved system for generating confocal images of in-vivo tissue which enables surgical treatment either to be localized to a small region of tissue being imaged, or to be non-localized over a region of tissue including that small region of tissue.

Another object of the present invention is to provide an improved system for generating through confocal optics images of in-vivo tissue which enables laser surgical treatment of the tissue being imaged, allows for evaluating the effectiveness of such treatment by simultaneously or sequentially imaging the treated tissue, and for modifying the operating parameters of the laser and/or confocal optics in subsequent treatments of the tissue.

Briefly described, the present invention embodies a system including a laser for producing a laser beam, and confocal optics for scanning and focusing the beam in tissue and collecting returned light from the tissue. A detector is provided which confocally detects the returned light and produces signals in accordance with the detected returned light representing confocal images. Responsive to the signals, such confocal images are visualized on a display. The system further includes a programmed controller for enabling the operator to select one or more cells of the tissue in the visualized confocal images for surgical treatment. The controller operates the laser and confocal optics in a first mode at a first set of operating parameters to treat the tissue when the confocal optics focus the laser beam at least one region associated with the selected cells in the tissue, but at all other times operates the laser and confocal optics in a second mode at a second set of operating parameters which does not damage the tissue.

The region may include at least one of the selected cells and other cells of the tissue surrounding the selected cell, thereby providing non-localized treatment. The region may also be localized to at least one of said selected cells, thereby providing localized treatment.

The above operating parameters may include the energy density, pulse width, duty cycle, power, or wavelength of the laser, and the scan rate, field of view, or depth of focus provided by the confocal optics. At the first set of operating parameters sufficient laser energy exposure is provided to the tissue to effect treatment of the tissue. All or some of the operating parameters may differ between the first and second sets of operating parameters.

The present invention also embodies an apparatus having a confocal imaging system which focuses a first laser beam through confocal optics to tissue and provides confocal images of the tissue. A treatment system is provided which focuses a second laser beam through the confocal optics coaxial with the first laser beam for treating one or more selected locations in the imaged tissue.

BRIEF DESCRIPTION OF THE DRAWINGS

The foregoing objects, features and advantages of the invention will become more apparent from a reading of the following description in connection with the accompanying drawings, in which.

DETAILED DESCRIPTION OF THE INVENTION

Figure 1:
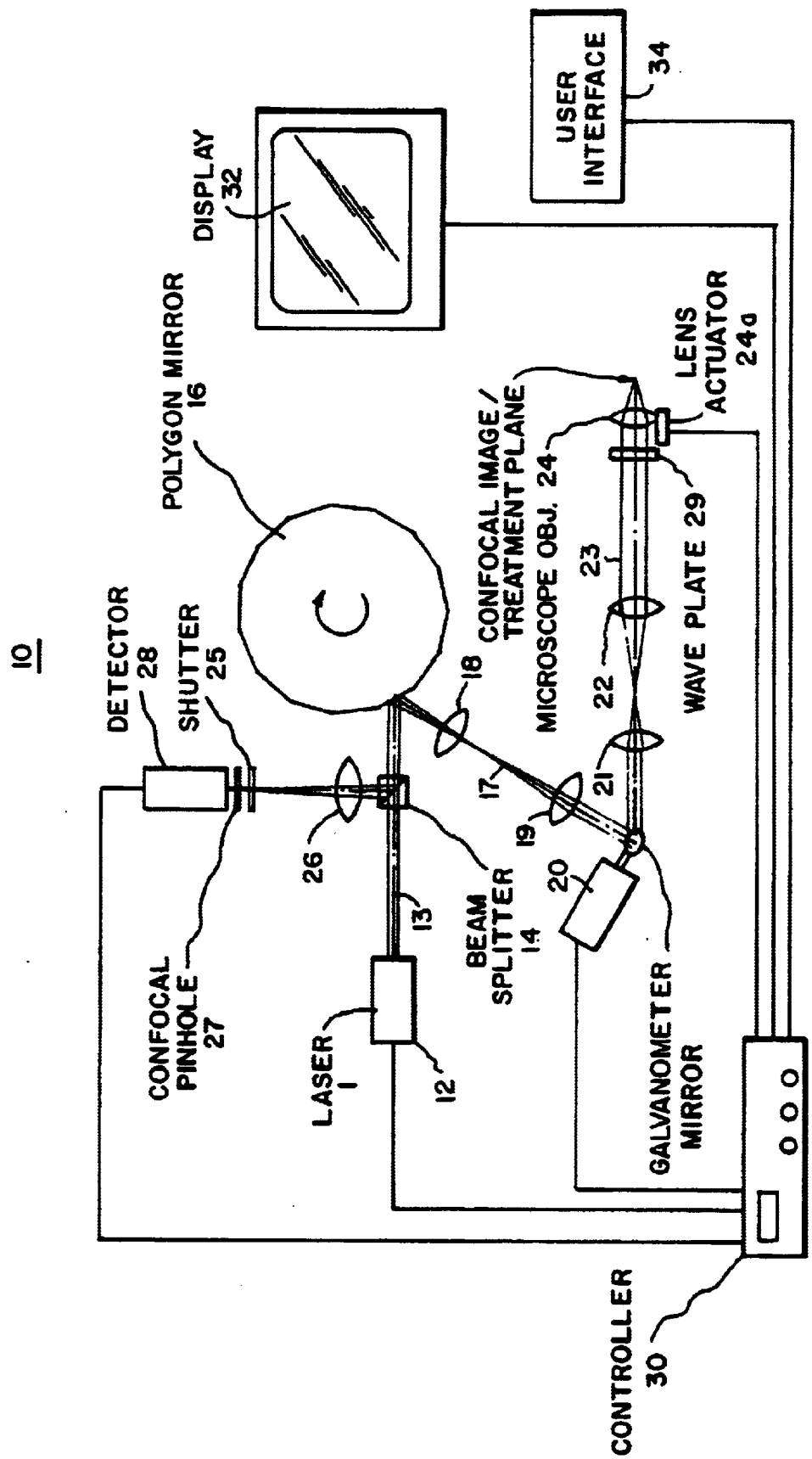
FIG. 1 is a block diagram of a system in accordance with the present invention.

Referring now to FIG. 1, a system 10 of the present invention is shown. System 10 includes a first laser 12

(Laser 1) for producing light (a laser beam) at an infrared wavelength along a path 13 through beam-splitter 14 onto a rotating polygon mirror 16. Polygon mirror 16 has a plurality of mirror facets to reflect the beam from laser 12 at varying angles responsive to the rotation of mirror 16, i.e., to repeatedly scan the beam. The reflected beam from rotating polygon mirror 16 travels along a path 17 through relay and focusing lenses 18 and 19 onto a galvanometer mirror 20. Lenses 18 and 19 image the beam reflected by the polygon mirror facet onto galvanometer mirror 20. Galvanometer mirror 20 reflects the beam incident thereto at a controlled angle through lenses 21 and 22 along a path 23 to an objective focusing lens 24. Lenses 21 and 22 image the beam reflected by galvanometer mirror 20 onto objective lens 24. A quarter-wave plate 29 is provided in path 23 between lens 22 and objective lens 24. The beam through objective lens 24 is then focused at a spot at the confocal image/treatment plane in a tissue of a patient. This tissue may represent any natural or surgically exposed surface of the body of the patent, such as skin, teeth, oral mucosa, cervix, or internal body tissue during surgery.

The returned reflected light from the tissue is collected by objective lens 24. The reflected light travels from objective lens 24 through lenses 22 and 21 to galvanometer mirror 20. Mirror 20 reflects the light to rotating polygon mirror 16 via lenses 19 and 18, and then polygon mirror 16 reflects the light onto beam-splitter 14. Beam-splitter 14 reflects the light through lens 26 onto a detector 28, via a confocal pinhole 27 to produce a confocal image on detector 28. The detector receives the scattered light returned from tissue representing the confocal image. Detector 28 may be a solid-state detector, such as an avalanche photodiode. The above described components provide a confocal imaging subsystem in system 10, and such components may be situated within a confocal head of a microscope.

Preferably, the imaging laser beam is linearly polarized, and beam-splitter 14 is a polarizing beam-splitter. Quarter-wave plate 29 is located in path 23 between lenses 22 and 24 for converting specularly reflected light from the tissue to a polarization state orthogonal to the incident illumination of the laser beam to the tissue; this orthogonally polarized light is reflected by beam-splitter 14 to detector 28. Optionally, a shutter 25 may be placed in front of detector 28 to protect detector 28 from possible damage from the light returned from the tissue via beam-splitter 14. Shutter 25 may be a mechanical shutter, liquid crystal shutter, absorptive filter, or other type of similar optically protective material or mechanism.

The rotating polygon mirror 16 and galvanometer mirror 20 provide a scanning mechanism in system 10 for scanning the beam of laser 12 in two orthogonal dimensions through the tissue. However, other scanning mechanisms may be used, such as two galvanometer mirrors which direct the beam of laser 12 along paths 17 and 23, respectively, holographic or diffractive scanning, or transverse mechanical scanning of objective lens 24. Further, a mechanical actuator stage 24a may be provided to move objective lens 24 along its optical axis to control the depth of the focused spot in the tissue. In system 10, the scanning mechanism, lenses 18, 19, 21, 22 and 24, plate 29, beam-splitter 14, shutter 25, and pinhole 27, are referred generally to as confocal optics.

A programmed controller 30, such as a personal computer, controls the operation of system 10. Controller 30 can enable laser 12 and control the laser's operating parameters, such as the energy density (or intensity), pulse width, power, duty cycle, and wavelength, of the beam emitted from laser 12. Controller 30 also controls the operating (or beam delivery) parameters of the confocal optics, such as the scan rate of the scanning mechanism, depth of focus in the tissue, setting of shutter 25, and area of illumination (scan width and height), i.e., the field of view of the confocal optics. The scanning mechanism is controlled by controller 30 by enabling the rotation of polygon mirror 16 via a motor (not shown), and the angular position of galvanometer mirror 20. The controller 30 controls the depth of focus in the tissue of the laser beam by setting the position of the objective lens 24 via actuator stage 24a. The controller may monitor the position of the scanning mechanism and/or lens 24 during scanning, or direct the scanning mechanism and/or lens 24 to provide the focused spot at a specific position in the tissue. Preferably, the controller operates the laser and confocal optics in a visualizing mode where the laser does not damage the tissue, and in a treatment mode to treat the tissue. Detector 28 provides controller 30 signals representing confocal images. As the scanning mechanism scans the tissue, successive frames of confocal images are provided in real-time to controller 30 from detector 28. The controller 30 drives a display 32 to display as a raster scan the confocal images. The displayed confocal image is a two-dimensional digital image composed of an x-y pixel array.

A user interface 34, such as a mouse, keyboard, light pen, or the like, allows an operator to input to controller 30 selected cell or cells (a region of cells) shown on display 32 for subsequent surgical treatment. Controller 30 is programmed to translate the x-y pixel coordinates of the locations of selected cell or cells on display 32 into terms of the mechanical position of the scanning mechanism of system 10, i.e., the position of mirrors 20 and 16 when focusing the beam from laser 12 at the locations of such cells. The raster scan of the confocal image on display 32 is on a time-scale corresponding with the position of scanning through tissue.

In operation, an operator, such as a physician, first manually positions the confocal optics of system 10 such that objective lens 24 is placed over the tissue to be treated. Preferably, the confocal optics are mechanically stabilized to the tissue surface, such as described in U.S. patent application Ser. No. 08/942,431, filed Oct. 1, 1997 by James M. Zavislan now U.S. Pat. No. 6,424,852 issued Jul. 23, 2002. The controller operates the laser 12 and confocal optics in a visualizing mode at a set of operating parameters (visualizing mode parameters) in which the energy exposure of the tissue to the beam does not damage the tissue. The confocal optics provide controller 30, via signals from detector 28, confocal images of the tissue. On display 32, the confocal imaged section of the tissue appears as a microscopic picture showing surface or subsurface cells of the tissue. The operator can adjust the depth of the tissue being imaged by fixing the position of objective lens 24 and then moving the tissue, or by restraining the tissue and moving the objective lens 24 along its optical axis via actuator 24a. In this manner, the operator visualizes the tissue to identify the nominal tissue area to be treated.

Next, the operator identifies a cell or groups of cells having histological signatures in the displayed confocal images of the tissue. A histological signature is a spatial or spectral characteristic which identifies the cells in the displayed image. Spectral characteristics refer to fluorescent or absorptive features of the cells in the displayed image, such as a melanocyte which appears fluorescent in dermal tissue. Spatial characteristics refer to the specific geometry or orientation of cells, such as, for example, nucleus to cytoplasm area ratio, the shape of melanocytic dendrites, or birefringence of tissue structures.

After identification of cells, the operator selects (or targets) the cell or groups of cells in the displayed image via user interface 34, i.e., such cells displaying certain histological features. Controller 30 translates those selected cell or cells in terms of the position of the scanning mechanism when focusing the beam from laser 12 at locations of such cells. The user may also select via interface 34 the set of operating parameters of laser 12 and the confocal optics (treatment mode parameters) during a treatment mode to provide the desired energy exposure of the tissue to effect surgical treatment. By setting a different scan rate of the confocal optics between treatment and visualizing modes, the time of the laser at each selected location can be increased or decreased during treatment. However, if desired, the operating parameters of the confocal optics may be the same for both treatment and visualizing modes.

System 10 can perform at each selected location either localized or non-localized treatment of tissue depending on the treatment mode parameters and the concentration or distribution of laser energy exposure to the tissue. Energy exposure is defined as the product of the laser power and the average time at a selected location in the tissue. At each location of selected cell or cells in localized treatment, laser 12 and the confocal optics concentrate the energy or optical effect to a specific targeted small region of tissue that generally includes the selected cell or cells. This small region may be a volume of tissue of approximately 20 micrometers by 20 micrometers by 20 micrometers or less. For localized treatment of subsurface tissue, the wavelength of the laser beam during treatment mode should be chosen to provide concentration of energy at the desired depth of treatment in the tissue. For localized treatment of surface tissue, the wavelength of the laser beam during treatment mode should be chosen which can selectively heat or ablate the tissue, photo-chemically or photo-mechanically effect the issue, or photo-activate a drug in the tissue. Such localized treatment is described later in more detail.

At each location of selected cell or cells in non-localized treatment, laser 12 and the confocal optics distribute the energy or optical effect over a region of tissue greater than the small subregion that generally includes the selected cell or cells. This region thus includes the cells surrounding the selected cell or cells. Such surrounding cells may or not be confocally imaged. Non-localized treatment is useful where the selected cells define a histological marker of a larger region desired to be treated. The wavelength of laser 12 and the focus of the beam should be chosen during treatment mode to distribute treatment to the region, which may or may not be within the field of view of the confocal optics. Distribution of the laser energy over the region of tissue may by either a single laser shot for gross treatment (such as coagulation) of the tissue region, or multiple laser shots at several locations within the region.

To perform surgical treatment, the operation of laser 12 is modulated by controller 30 between its visualizing and treatment mode parameters during a scan to implement localized or non-localized treatment at the selected locations. Also, the operation of the confocal optics may be either modulated between their visualizing and treatment mode parameters, or maintained constant during a scan at their treatment mode parameters. Specifically, controller operates the laser and the confocal optics at the treatment mode parameters when the scanning mechanism locates the focused spot at such positions associated with the selected cell or cells, but at all other times operates the laser and confocal optics at the visualizing mode parameters which do not cause tissue damage. If desired, treatment may occur at selected locations over multiple scans. The increased energy exposure of the tissue at the selected locations may cause a thermal effect on the selected cells, such as thermolysis.

During treatment, controller 30 may operate shutter 25 to protect detector 28 when beam-splitter 14 reflects sufficiently at the wavelength of the treating laser beam such that excessive power is received in light at detector 28. The operator may simultaneously view the tissue during treatment on display 32 or sequentially between treatments at different locations in the tissue.

After treatment, with laser 12 and confocal optics in a visualizing mode, the operator views confocal images of the treated tissue on display 34 to determine the effectiveness of the localized or non-localized treatment. In non-localized treatment, the selected cell or cells serve as a marker for treatment in the treated region of tissue. If the treatment was not sufficiently effective, i.e., the tissue received an insufficient energy exposure, the operator can repeat the treatment at the same or different treatment mode parameters, such as increasing the energy density of laser 12. If the operator determines that the treatment was effective, the operator may select another area of tissue for treatment.

In surgical treatment of dermal tissue, system 10 allows an operator to select individual cells or groups of cells for localized or non-localized treatment in the layers of the epithelia, supporting stroma, or in capillaries flowing through the skin. For example, basal cells, squamous cells, melanocytes, or collagen can be treated. Further, confocal images of the skin can show individual cells in blood moving through capillaries. As cells move through a capillary, they can individually be selected by the operator and treated. Further, controller 34 may be programmed to identify histological signatures of cell or cells, automatically select such cell or cells for treatment, and then treats the cells in the manner so described.

System 10 may effect localized surgical treatment of tissue by operating laser 12 at an energy density and wavelength sufficient to cause photo-chemical-changes or photolysis. For example, laser 12 may be operated in a mode to provide two-photon treatment by emitting high energy femtosecond laser pulses. Such laser pulses cause second-order light effects (two-photon) at selected cell or cells which effect treatment by destroying the cells. This destructive cellular effect is described in "Cellular response to near-infrared femtosecond laser pulses in two-photon microscopes" by König, et al., Optics Letters, Vol. 22, No. 2, Jan. 15, 1997.

Figure 2:
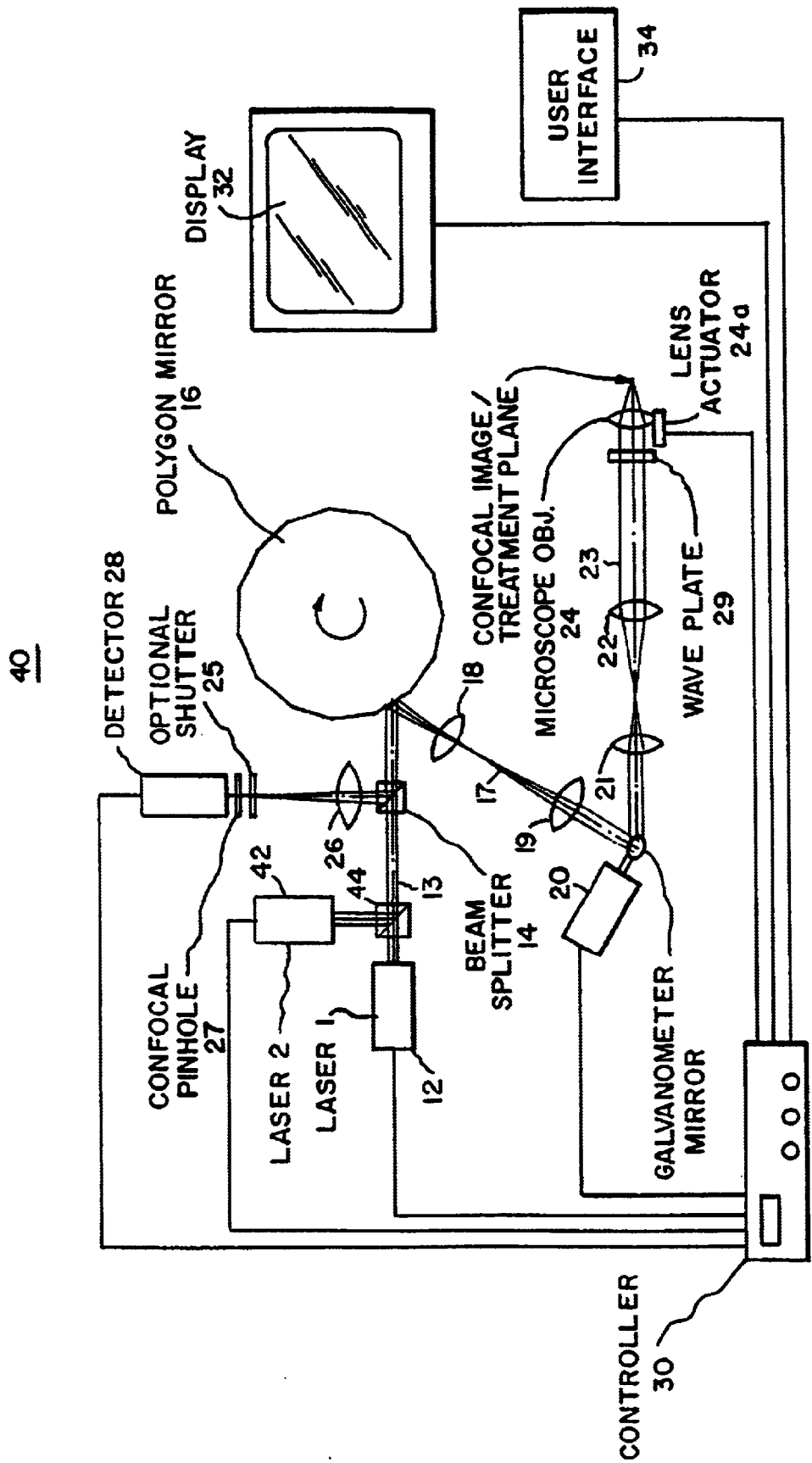
FIG. 2 is a block diagram of another system in accordance with the present invention.

Referring to FIG. 2, a system 40 of the present invention is shown. System 40 is identical with system 10, except that another laser 42 is used to implement treatment instead of laser 12. Thus, controller 30 in system 40 preferably, in conjunction with the confocal optics, operates laser 12 only at operating parameters (i.e., its visualizing mode parameters) which do not cause damage to the tissue. Laser 42 provide light (a laser beam) at either the same wavelength as laser 12 during treatment or a different wavelength. The wavelength of laser 42 may be from the extreme ultraviolet to the infrared, 192 nanometers to 10.6 micrometers. When operated in this range, the refractive objective lens 24 and other lenses of the confocal optics may be replaced by optical elements which operate in this wavelength range, such as reflective surface or transmissive refractive materials at both the treatment beam (from laser 42) and the visualizing beam (from laser 12) wavelengths. The beam from laser 42 when enabled is reflected by a beam-splitter 44 through the confocal optics coaxially with the beam from laser 12, and the beam from laser 12 when enabled passes through beam-splitter 44 along path 13. Similar to the operating of laser 12, controller 30 can enable laser 42 and control the laser's operating parameters. The focused spot of the beam from laser 42 forms in the vicinity of the focused spot of the beam from laser 12 in the tissue.

The operation of system 40 is the same as that of system 10 for producing confocal images and for selecting and treating tissue, except that controller 30 instead of operating laser 12 to effect localized or non-localized treatment of tissue, operates laser 42 as to effect such treatment. Laser 42, beam-splitter 44, and the confocal optics, which the beam from laser 42 is incident upon, provides a treatment subsystem in system 40 controlled by controller 30.

Figure 3:
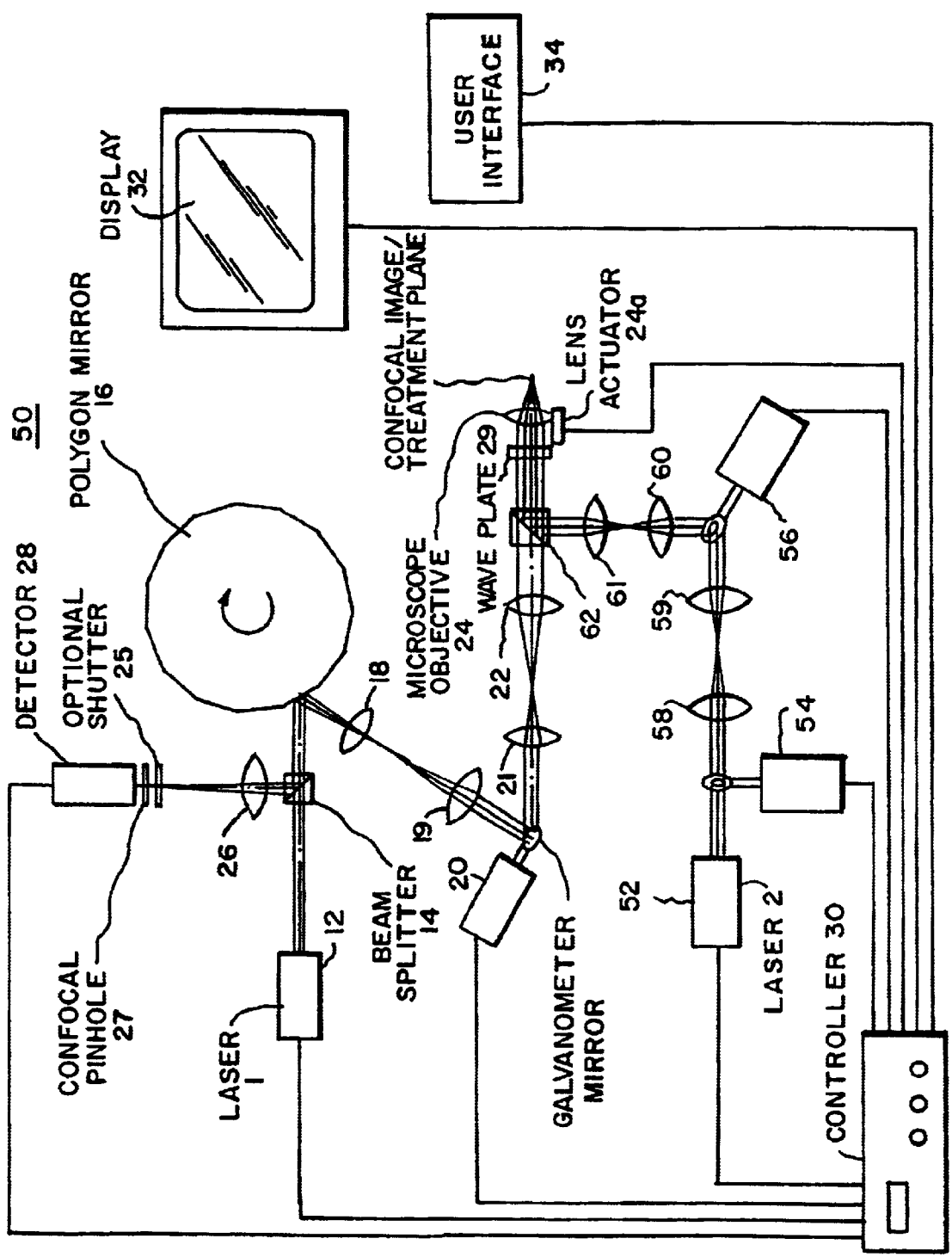
FIG. 3 is a block diagram of a further system in accordance with the present invention.

Referring to FIG. 3, a system 50 of the present invention is shown. System 50 is identical to system 10, except that another laser 52 is used to implement treatment instead of laser 12. Controller 30 in system 50 preferably, in conjunction with the confocal optics, operates laser 12 only at operating parameters (i.e., its visualizing mode parameters) which do not cause damage to the tissue. Laser 52 provide light (a laser beam) at either the same wavelength as laser 12 during treatment or a different wavelength. The wavelength of laser 52 may be from the extreme ultraviolet to the infrared, 192 nanometers to 10.6 micrometers. When operated in this range, the refractive objective lens 24 and other lenses of the confocal optics may be replaced by optical elements which operate in this wavelength range, such as reflective surface or transmissive refractive materials at both the treatment beam (from laser 52) and the visualizing beam (from laser 12) wavelengths.

Two galvanometer mirrors 54 and 56 provide a scanning mechanism for the beam from laser 52. Relay and focusing lenses 58 and 59 are located in the path of the from mirror 54 to image the light from mirror 54 onto mirror 56. Relay and focusing lens 60 and 61 are located in the path of the beam reflected from mirror 56 to image the light from mirror 56 onto a beam-splitter 62. Beam-splitter 62 reflects the beam from mirror 56 coaxially with the path of the beam from laser 12 through the confocal optics, i.e., objective lens 24. Similar to the operating of laser 12, controller 30 can enable laser 52 and control the laser's operating parameters. The focused spot of the beam from laser 52 forms in the vicinity of the focused spot of the beam from laser 12 in the tissue. Laser 52, mirror 54 and 56, lenses 58–61, and beam-splitter 62, and objective lens 24 provides a treatment subsystem in system 40 controlled by controller 30.

In operation, system 50 operates the same as system 10 for producing confocal images and for selecting and treating tissue, except: After the operator has selected the cell or cells to be surgically treated, controller 30 translates the x-y position of the cells on display 32 in terms of the positions of mirrors 54 and 56. Mirror 54 and 56 then are positioned to selectively project the beam from laser 52 at the location of such selected cell or cells, while laser 52 is operated by controller 30 at treatment mode parameters to effect treatment.

Both systems 40 or 50 may be operated to provide the same localized and non-localized treatment as discussed in system 10 using their respective lasers 42 or 52. In addition, systems 40 and 50 can provide localized photo-drug activation of selected confocally imaged cells in which lasers 42 or 52, respectively, are at operating parameters (wavelength) during treatment which photoactivate a photo-dynamic drug present in such cells. This drug is non-active when introduced into the patient prior to treatment, but activated in tissue by the treating laser beam. Such photo-dynamic drugs are often used in certain cancer therapy. The activation by the treating laser beam may also be done by the two-photon process, as described above.

Systems 10, 40 or 50 may be used to perform ablation on confocally imaged areas on the surface of skin, such as in the removal of dermal plaque or basal cell carcinoma. These systems may interatively treat surface tissue to successively remove portions of the plaque until the plaque has been entirely ablated. Between each iteration, the skin surface is confocally imaged on display 32 to determine the location of the next treatment. In systems 40 or 50, their respective treating lasers 42 or 52 provide a laser beam which is absorptive. Lasers 42 or 52 may be an excimer, holmium, erbium or $CO_2$ laser. In system 10, laser 12 to effect treatment may be operated at a high peak power.

Further, systems 10, 40 or 50, may be used to perform localized selective thermolysis in which the laser beam effecting treatment operates at a wavelength which is selectively absorbed by certain chromophors of selected cell or cells in the confocally imaged tissue, but only nominally absorbed, i.e., non-damaging, to surrounding cells. Thus, energy of the treating beam is localized to the cells to be treated. Localized selective thermolysis by a laser is described in the publication by Jeffrey Dover and Kenneth Arndt,"Illustrated Cutaneous Laser Surgery, A Practitioner's Guide," Appleton and Lange, Norwalk, Conn. (1990), page 17.

Absent controller 30, display 32 and user interface 34, systems 10, 40 or 50 may be adapted to be hand-held by an operator.

From the foregoing description, it will be apparent that there has been provided an improved system for cellular surgery utilizing confocal microscopy. Variations and modifications in the herein described system in accordance with the invention will undoubted suggest themselves to those skilled in the art. Accordingly, the foregoing description should be taken as illustrative and not in a limiting sense.

What is claimed is:

1. A system for cellular surgery in tissue comprising:
   common optics for scanning and focusing an imaging beam in or on the tissue and for collecting reflected light from the tissue;
   means for detecting said reflected light, and producing at least one image of a section of the tissue;
   means for identifying a histological signature from said image;
   means responsive to said signature for selecting one or more cells of the tissue in said image to target for surgical treatment; and
   means utilizing at least part of said optics to treat the tissue.

2. An apparatus for treating tissue comprising:
   an imaging system which focuses a first laser beam through optics to tissue and receives returned light from the tissue to provide images of one or more sections of the tissue; and
   a treatment system which focuses a second laser beam through at least some of said optics with the first laser beam for treating one or more selected locations in the imaged tissue in accordance with histological signatures from said image.

3. The apparatus according to claim 2 wherein said imaging system comprises:
   a first laser for producing said first laser beam in which said optics scan and focus said first laser beam in the tissue and collect reflected light from the tissue;

means for detecting said returned light and producing signals in accordance with said detected returned light representing said images; and means responsive to said signals for visualizing said images of the tissue.

4. A method for cellular surgery in tissue comprising the steps of:

providing a laser which produces an illumination beam;

scanning and focusing the beam in tissue and collecting returned light from said tissue with the aid of optics;

detecting said returned light and producing signals in accordance with said detected returned light representing images having histological signatures of said tissue;

visualizing said images of said tissue in accordance with said signals;

targeting in response to said histological signatures one or more cells of said tissue in said visualized images for surgical treatment; and operating said laser between a first mode to expose said tissue to the energy of said beam sufficient to treat said tissue and a second mode to visualize said tissue without damaging said tissue, in which said laser and optics are in said first mode when said optics focuses the beam at least one region in the tissue associated with said targeted cells, and said laser and optics are in said second mode at all other times.

5. The method according to claim 4 wherein said region includes at least one of said targeted cells and other cells of said tissue surrounding said one of said targeted cells.

6. The method according to claim 4 wherein said region is localized to at least one of said targeted cells.

7. An apparatus for cellular surgery in tissue comprising:

a laser for producing a beam;

optics for scanning and focusing the beam in tissue and collecting returned reflected light from the tissue;

a detector which receives said returned reflected light and produces signals, in accordance with said detected returned light, representing images;

a display which enables said images of the tissue to be visualized responsive to said signals;

a controller which enables the selection of one or more cells in at least one of said visualized images on said display to target for surgical treatment; and said controller operating said laser and optics in a first mode to treat the tissue when said optics focuses the beam at the location of said selected cells in the tissue, and at all other times operating said laser and confocal optics in a second mode to not damage the tissue.

8. A system for cellular surgery of tissue comprising:

a light source for producing a beam;

optics for scanning the beam along a path in two-dimensions;

a lens in said path for focusing the beam to the tissue and said lens collects returned light from the tissue;

image detection means for receiving said returned light via said optics to provide an image of the tissue;

means for controlling the position of said lens to change the depth of focus of the beam in the tissue;

means for selecting one or more cells in the image to target for treatment; and means for operating said light source to treat the tissue according to the position of the cells in the image in which said tissue represents exposed tissue located in or on the body of the patient.

9. A system for cellular surgery of tissue comprising:

a first light source for producing a beam;

optics for scanning the beam along a path in two-dimensions;

a lens in said path for focusing the beam to the tissue in which said lens collects returned light from the tissue;

image detection means for receiving said returned light via said optics to provide at least one image of a section of the tissue;

means for controlling the position of said lens to change the depth of focus of the beam in the tissue;

means for selecting one or more cells in the image to target for treatment;

a second light source co-axial with at least said beam incident said lens; and means for operating said second light source to treat the tissue according to the position of the cells in the image in which the tissue represents exposed tissue located in or on the body of the patient.

* * * * *